United States Patent [19]

Peglion et al.

[11] Patent Number: 5,665,765

[45] Date of Patent: Sep. 9, 1997

[54] 5,6,7,8-TETRAHYDRONAPHTHO[2,3-B]FURAN AND INDANO[5,6-B]FURAN AMINE COMPOUNDS

[75] Inventors: Jean-Louis Peglion, Le Vesinet; Joel Vian, Chaville; Aimée Dessinges, Thiais; Mark Millan, Le Peco; Valérie Audinot, Poissy, all of France

[73] Assignee: Adir et Compagnie, Courbevoie, France

[21] Appl. No.: 720,039

[22] Filed: Sep. 27, 1996

[30] Foreign Application Priority Data

Sep. 29, 1995 [FR] France .................... 95 11446

[51] Int. Cl.[6] ................ A61K 31/34; C07D 307/92
[52] U.S. Cl. .................. 514/468; 514/414; 548/454; 549/458
[58] Field of Search ............ 549/458; 548/454; 514/414, 468

[56] References Cited

U.S. PATENT DOCUMENTS

| 4,851,429 | 7/1989 | Peglion et al. ............ 549/458 |
| 4,863,951 | 9/1989 | Peglion et al. ............ 549/458 |

*Primary Examiner*—Bernard Dentz
*Attorney, Agent, or Firm*—The Firm of Gordon W. Hueschen

[57] ABSTRACT

New compounds of formula:

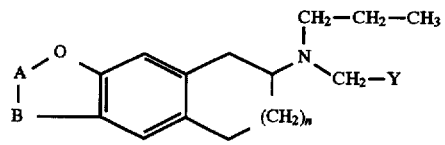

wherein:

A–B, n and Y are as defined in the description, their optical isomers and physiologically tolerable salts thereof with appropriate acids.

The products of the invention may be used as medicaments.

7 Claims, No Drawings

5,6,7,8-TETRAHYDRONAPHTHO[2,3-B] FURAN AND INDANO[5,6-B]FURAN AMINE COMPOUNDS

The present invention relates to new 5,6,7,8-tetrahydronaphtho[2,3-b]furan and indano[5,6-b]furan amine compounds.

It relates more especially compounds of formula I:

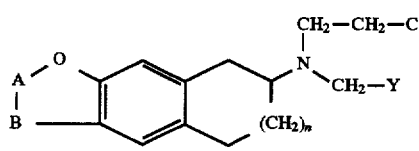

wherein:

A—B represents CH=CH or $CH_2$—$CH_2$;

n represents zero or one; and

Y represents:
an alkenyl radical containing from 2 to 10 carbon atoms in straight or branched chain;
a ω-(cycloalkyl)alkyl, ω-(methylcycloalkyl)alkyl or ω,ω-(dicycloalkyl)alkyl radical in each of which each cycloalkyl group contains from 3 to 7 carbon atoms and the alkyl moiety contains from 1 to 4 carbon atoms in straight or branched chain; or
a radical of formula:

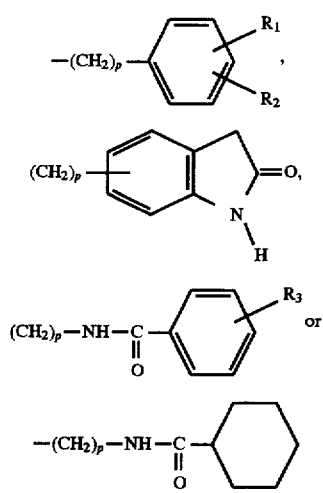

wherein:

p is an integer of from 1 to 4 inclusive, $R_1$ represents a hydrogen or halogen atom, or a hydroxy or methoxy radical, $R_2$ represents a halogen atom, a hydroxy, ($C_1$-$C_5$)alkoxy or phenyl radical or a group of formula: —NH—CO—$CH_3$, —NH—CO—$CF_3$ or —NH—$SO_2$—$CH_3$, and $R_3$ represents a halogen atom or a ($C_1$-$C_5$)alkoxy, trifluoromethyl, cyano, phenyl, p-aminophenyl or p-acetylphenyl radical;

in racemic form or in the form of optical isomers; and their addition salts with a pharmaceutically acceptable acid.

The prior art is illustrated especially by the Patent Specifications EP 0 286 515 and 0 286 516 which relate, inter alia, to 5,6,7,8-tetrahydronaphtho[2,3-b]furan amine compounds that The prior art is illustrated especially by the Patent Specifications EP 0 286 515 and 0 286 516 which relate, inter alia, to 5,6,7,8-tetrahydronaphtho[2,3-b]furan amine compounds that behave like dopaminergic substances and have an antidepressant, anti-aggressive and psychostimulating activity.

Research carried out in the departments of the Applicant has demonstrated that by modifying the substituents of the amine function, a reinforcement of the dopaminergic properties of those products has been possible while making them more specific and selective, enabling the said products to have reduced side effects.

Currently, the substances used therapeutically for the treatment of disorders in which the dopaminergic system is implicated are not selective and all bind very strongly to the $D_2$ receptor, whether they are dopaminergic blockers (used in disorders associated with hyperactivity of that neurotransmitter as occur, for example, in schizophrenia) or dopaminergic activators (used in disorders associated with hypoactivity as occur in Parkinson's disease, for example). However, those $D_2$ dopaminergic blockers or activators have numerous side effects: tardive dyskinesia, hyperprolactinaemia, amenorrhoea in the case of the former, and cardiovascular and motor effects in the case of the latter.

The recent discovery of a new dopamine receptor, called the $D_3$ receptor, the concentration of which is very significant in the limbic system but very low in the nigrostriated nucleus and in the lactotrophic cells, encourages research into new medicaments that act on the dopaminergic system but that have as a preferential target the $D_3$ receptor and are thus exempt from the side effects typically associated with the $D_2$ receptor as mentioned above.

The structural modifications of the products of the prior art mentioned above have resulted in the compounds forming the subject of the present invention, which differ from the products of the Patent Specifications EP 0 286 515 and 0 286 516 both in their chemical structure and in their pharmacological and therapeutic properties.

Indeed, studies carried out in vitro (binding to cloned human $D_2$ and $D_3$ receptors) with the compounds of the present invention demonstrate that the latter behave like ligands that have a high affinity for the $D_3$ dopaminergic receptors while having little affinity for the $D_2$ dopaminergic receptors, which is not true of the compounds forming the subject of the Patent Specifications EP 0 286 515 and 0 286 516.

That selectivity makes the compounds of the present invention valuable especially for use as medicaments that act on the dopaminergic system in Parkinson's disease (J. Neur. Transm., 1993, 94, 11–19), memory disorders (Nature, 1990, 347, 146–151), drug abuse (Science, 1993, 260, 1814), depression and as an antipsychotic.

The present invention relates also to a process for the preparation of compounds of formula I, characterised in that a secondary amine of formula II:

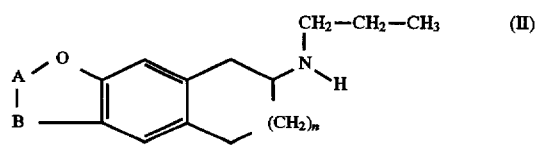

wherein A—B and n are as defined above, is reacted with a halogenated compound of formula III:

$$X\text{—}CH_2\text{—}Y \quad \text{(III)}$$

wherein:

Y is as defined above and

X represents a chlorine, bromine or iodine atom, in an alkaline medium such as $Na_2CO_3/H_2O$ or $K_2CO_3/CH_3CN$;

or with a compound of formula IV:

$$\begin{array}{c} HC\text{—}Y \\ \parallel \\ O \end{array} \quad \text{(IV)}$$

wherein Y is as defined above, in a reductive medium, for example in the presence of sodium triacetoxyborohydride in acetic acid;

or with an acylating compound of formula V:

$$\begin{array}{c} Z\text{—}C\text{—}Y \\ \parallel \\ O \end{array} \quad \text{(V)}$$

wherein:

Y is as defined above and

Z represents a hydroxy radical or a chlorine atom, and the resulting compound of formula VI:

(VI) [structure with $CH_2$—$CH_2$—$CH_3$, N, C—Y, O, A, B, $(CH_2)_n$]

wherein A—B, n and Y are as defined above is reduced.

The acylation of the compound of formula II with the compound of formula V is carried out especially advantageously, in the case where Z represents a hydroxy radical, in a dichloromethane medium in the presence of carbonyldiimidazole and, in the case where Z represents a chlorine atom, in a dichloromethane medium in the presence of N,N-diisopropylethylamine. The reduction of the compound of formula VI is suitably carried out using either lithium aluminium hydride ($LiAlH_4$) or dimethylborane sulfide as reducing agent.

The starting materials of formula II were prepared from the corresponding primary amines, which were themselves obtained according to the process described in U.S. Pat. No. 4,874,878 for the preparation of dl-7-amino-2,3,5,6,7,8-hexahydronaphtho[2,3-b]furan.

The optically active forms of the compounds of formula I were obtained either from the optically active forms of the starting materials of formula II, or by resolving the racemic forms of the compounds of formula I, according to methods known from the literature.

The present invention relates also to pharmaceutical compositions comprising as active ingredient a compound of formula I or a physiologically tolerable salt thereof, mixed with or in association with one or more appropriate pharmaceutical excipients.

The pharmaceutical compositions so obtained are generally presented in a dosage form containing from 0.5 to 25 mg of active ingredient. They may, for example, be in the form of tablets, dragées, gelatin capsules, suppositories or injectable or drinkable solutions and may be administered by the oral, rectal or parenteral route.

The posology may vary according to the age and weight of the patient, the administration route, the nature of the disorder and associated treatments, and ranges from 0.5 to 25 mg of active ingredient from 1 to 3 times per day.

The following Examples, which are given as non-limiting examples, illustrate the present invention. The melting points were determined either using a Kofler hot plate (K), or a hot plate under a microscope (MK). The proton nuclear magnetic resonance spectra (NMR) were carried out at 200 MHz, unless indicated otherwise.

EXAMPLE 1

(7RS)-7-{N-[2-(3,4-dimethoxyphenyl)ethyl]-N-propylamino}-5,6,7,8-tetrahydronaphtho[2,3-b]2,3-dihydrofuran, and its (dl)-dibenzoyltartrate Step A: (7RS)-N-propyl-N-(5,6,7,8-tetrahydronaphtho[2,3-b]2,3-dihydrofuran-7-yl)-(3,4-dimethoxyphenyl)acetamide.

3.6 g of carbonyldiimidazole are added in portions to 4.3 g of 3,4-dimethoxyphenylacetic acid dissolved in 50 ml of dichloromethane. After two hours' stirring at room temperature, a solution of 5 g of 7-N-propylamino-5,6,7,8-tetrahydronaphtho[2,3-b]2,3-dihydrofuran in 50 ml of dichloromethane is poured in dropwise. After 18 hours' stirring at room temperature, the reaction mixture is washed in succession with a normal sodium hydroxide solution, a normal hydrochloric acid solution and a saturated sodium chloride solution. After separation and evaporation of the solvent in a rotary evaporator, 4.5 g of an oil that corresponds to the expected compound are obtained. Yield: 55%.

Step B: Title compound

A solution of 4.5 g of the compound obtained in Step A in 80 ml of tetrahydrofuran is added dropwise to a suspension of 0.85 g of lithium aluminum hydride in 40 ml of tetrahydrofuran. After 18 hours' reflux, the mixture is hydrolysed in succession with 0.6 ml of water, 0.5 ml of 20% sodium hydroxide solution and then 2.2 ml of water. After filtration of the mineral salts, the filtrate is evaporated in a rotary evaporator to obtain 2.5 g of the title product. The salt is obtained by the addition of 119 ml of a 2% solution of (dl)-dibenzoyltartaric acid in ethanol. After evaporation of the solvent in vacuo and crystallisation in water, 3.8 g of the (dl)-dibenzoyltartrate of (7R8)-7-{N-[2-(3,4-dimethoxyphenyl)ethyl]-N-propylamino}-5,6,7,8-tetrahydronaphtho[2,3-b]2,3-dihydrofuran are obtained, m.p. (K): 100°–105° C.; Yield: 46%.

NMR (DMSO d6)

$^1$H spectrum: 7.95 ppm (d,4H); 7.65 ppm (t,2H); 7.5 ppm (t,4H); 6.85 ppm (m,2H); 6.80 ppm (d,1H); 6.75 ppm (d, 1H); 6.45 ppm (s,1H); 5.7 ppm (s,2H); 4.45 ppm (t,2H); 3.7 ppm (2s,6H); 3.3 ppm (m,1H); 3.10 ppm (t,2H); 3.15 to 2.60 ppm (m,10H); 2.05 ppm (m,1H); 1.75 to 1.45 ppm (m,3H); 0.8 ppm (t,3H); exchangeables not clearly displayed.

EXAMPLE 2

(7RS)-7-{N-[2-(4-flouorophenyl)ethyl]-N-propylamino}-5,6,7,8-tetrahydronaphtho[2,3-b]-2,3-dihydrofuran and its (dl)-dibenzoyltartrate This compound is obtained as described in Example 1, with the replacement of the 3,4-dimethoxyphenylacetic acid in Step A of Example 1 with 4-fluorophenylacetic acid. The (dl)-dibenzoyltartrate obtained melts (K) at 115°–120° C.; yield: 43 %.

NMR (DMSO d6)

$^1$H spectrum 8.00 ppm (d,4H); 7.65 ppm (t,2H); 7.5 ppm (m,4H); 7.25 ppm (m,2H); 7.1 ppm (m,2H); 6.9 ppm (s, 1H); 6.4 ppm (s, 1H); 5.75 ppm (s,2H); 4.45 ppm (t,2H); 3.45 ppm (m, 1H); 3.20 to 2.80 ppm (m, 10H); 2.70 ppm (m,2H); 2.15 to 1.65 ppm (2m,4H); 0.8 ppm (t,3H); exchangeables not distinct.

EXAMPLE 3

(7RS)-7-{N-[2-(4-hydroxyphenyl)ethyl]-N-propylamino}-5,6,7,8-tetrahydronaphtho[2,3-b]2,3-dihydrofuran and its (dl)-dibenzoyltartrate Step A The method of Example 1 is used, in which the 3,4-dimethoxyphenylacetic acid has been replaced with 4-benzyloxyphenylacetic acid.

Step B

The method of Example 1, Step B is used.

Step C: Title compound

A solution of 9 g of the product obtained in the preceding Step in 200 ml of ethanol is hydrogenated for 6 hours at room temperature under 200 g of hydrogen in the presence of 0.8 g of 5% palladium-on-carbon. After the requisite quantity of hydrogen has been absorbed, the reaction mixture is filtered and concentrated in a rotary evaporator, and treated by the addition of 175 ml of a 2% solution of (dl)-dibenzoyltartaric acid in ethanol. After evaporation of the solvent in vacuo and crystallisation of the residue in water, 5.9 g of the expected (dl)-dibenzoyltartrate, which melts (K) at 130°–135° C., are obtained; yield: 50%.

NMR (DMSO d6)

$^1$H spectrum 8.00 ppm (d,4H); 7.65 ppm (t,2H); 7.5 ppm (m,4H); 7.0 ppm (d,2H); 6.85 ppm (s,1H); 6.65 ppm (d,2H); 6.45 ppm (s,1H); 5.75 ppm (s,2H); 4.45 ppm (t,2H); 3.45 ppm (m,1H); 3.2 to 2.6 ppm (m,12H); 2.15 ppm (m,1H); 1.80 to 1.50 ppm (m,3H); 0.8 ppm (t,3H); exchangeables not distinct.

EXAMPLE 4

(7RS)-7-{N-[2-(3-hydroxyphenyl)ethyl]-N-propylamino}-5,6,7,8-tetrahydronaphtho[2,3-b]2,3-dihydrofuran and its (dl)-dibenzoyltartrate The same methods as for Example 3 are used, except that in Step A the 4-benzyloxyphenylacetic acid is replaced with 3-benzyloxyphenylacetic acid. The (dl)-dibenzoyltartrate obtained melts (K) at 128°–132° C.; yield: 46%.

NMR (DMSO d6)

$^1$H spectrum 8.0 ppm (d,4H); 7.65 ppm (t,2H); 7.5 ppm (m,4H); 7.05 ppm (t,1H); 6.95 ppm (s,1H); 6.65 ppm (m,3H); 6.45 ppm (s,1H); 5.75 ppm (s,2H); 4.45 ppm (t,2H); 3.5 ppm ( m,1H); 3.30 to 2.50 ppm (m,12H); 2.15 ppm (m,1H); 1.80 to 1.50 ppm (m,3H); 0.85 ppm (t,3H exchangeables not distinct.

EXAMPLE 5

(7RS)-7-{N-[2-(3,4-dihydroxyphenyl)ethyl]-N-propylamino}-5,6,7,8-tetrahydronaphtho[2,3-b]2,3-dihydrofuran, and its (dl)-dibenzoyltartrate The procedure is as for Example 3, except that in Step A 3,4-dibenzyloxyphenylacetic acid is used instead of 4-benzyloxyphenylacetic acid. The (dl)-dibenzoyltartrate obtained melts (K) at 124°–128° C.; yield: 34%.

NMR (DMSO D6)

$^1$H spectrum 9.50 to 8.50 ppm (m,2H exchangeable with D$_2$O); 8.00 ppm (d,4H); 7.65 ppm (t,2H); 7.50 ppm (m,4H); 6.90 ppm (s,1H); 6.65 ppm (m,2H); 6.5 ppm (m,2H); 5.75 ppm (s,2H); 4.45 ppm (t,2H); 3.45 ppm (m,1H); 3.20 to 2.60 ppm (m,12H); 2.15 ppm (m,1H); 1.8 to 1.5 ppm (m,3H); 0.85 ppm (t,3H).

EXAMPLE 6

(7RS)-7-{N-[2-((3H)-indol-2-on-5-yl)ethyl]-N-propylamino}-5,6,7,8-tetrahydronaphtho[2,3-b]2,3-dihydrofuran, and its hydrochloride A mixture of 6 g of 5-(2-chloroethyl) (3H)-indol-2-one and 7.2 g of 7-N-propylamino-5,6,7,8-tetrahydronaphtho[2,3-b]2,3-dihydrofuran in a solution of 7.5 g of neutral sodium carbonate in 100 ml of water is heated at reflux for 5 hours. After a further addition of 6 g of the chlorine compound and refluxing again for 36 hours, the reaction mixture is cooled, extracted with ethyl acetate, separated and evaporated to dryness. 2.2 g of the expected product, purified by flash chromatography on silica using ethyl acetate as eluant, are obtained and converted into a salt in 22 ml of ethyl acetate by the addition of 2.8 ml of a 2.2N ethereal hydrogen chloride solution. The expected hydrochloride melts (K) at 178°–182° C.; yield: 19%.

NMR (DMSO d6)

$^1$H spectrum 10.55 to 10.35 ppm (m,2H exchangeable with D$_2$O); 7.20 ppm (d,1H); 7.10 ppm (d,1H); 6.95 ppm (s,1H); 6.75 ppm (d,1H); 6.55 ppm (s,1H); 4.45 ppm (t,2H); 3.65 ppm (m,1H); 3.5 ppm (s,2H); 3.40 to 2.90 ppm (m,10H); 2.8 ppm (m,2H); 2.30 ppm (m,1H); 1.80 ppm (m,3H); 0.95 ppm (t,3H).

EXAMPLE 7

(7RS)-7-{N-[3-((3H)-indol-2-on-5-yl)propyl]-N-propylamino}-5,6,7,8-tetrahydronaphtho[2,3-b]2,3-dihydrofuran This product was prepared by proceeding as in Example 6 but using 5-(3-chloropropyl)-(3H)-indol-2-one instead of 5-(2-chloroethyl)-(3H)-indol-2-one. The title product melts (K) at 126°–128° C.; yield: 27%.

NMR (CDCl$_3$)

$^1$H spectrum 8.1 ppm (m,1H); 7.05 ppm (m,2H); 6.9 ppm (1s,1H); 6.8 ppm (d,1H); 6.5 ppm (s,1H); 4.5 ppm (t,2H); 3.5 ppm (s,2H); 3.0 ppm (m,1H); 2.9 to 2.5 ppm (m,10H); 2.1 to 1.4 ppm (m,6H); 0.95 ppm (t,3H).

EXAMPLE 8

(7RS)-7-{N-[2-(3H)indol-2-on-4-yl)ethyl]-N-propylamino}-5,6,7,8-tetrahydronaphtho [2,3-b]2,3-dihydrofuran and its hydrochloride This product was prepared by proceeding as in Example 6 using appropriate starting materials. The hydrochloride obtained melts (MK) at 135°–150° C.

EXAMPLE 9

(7RS)-7-[N-(3-methylbut-2-enyl)-N-propylamino]-5,6,7,8-tetrahydronaphtho[2,3-b]2,3-dihydrofuran and its (dl)-dibenzoyltartrate General method A: (N-alkylation with a halogenated compound)

1.8 g (2.4 equivalents) of K$_2$CO$_3$ and 0.77 ml (1.2 equivalent) of 4-bromo-2-methylbut-2-ene are added at 25° C. to a solution of 1.3 g (5.6 mmol) of 7-(N-propylamino)-

5,6,7,8-tetrahydronaphtho[2,3-b]2,3-dihydrofuran in 20 ml of acetonitrile. The whole is stirred at room temperature for 2 hours, and then the solution is filtered and the filtrate is evaporated to dryness. The residue is taken up in $CH_2Cl_2$, washed with water, dried over $MgSO_4$, filtered and evaporated to dryness. 1.2 g of product, which is purified by flash chromatography on silica (eluant: $CH_2Cl_2$—$CH_3OH$—$NH_4OH$: 95-5-0.5), is obtained. 900 mg of base are obtained in the form of an oil.

47.2 ml (1 equivalent) of a 2% solution of (dl)-dibenzoyltataric acid in ethanol are added to 750 mg of base (2.5 mmol) dissolved in 40 ml of ethanol. The whole is stirred for 15 minutes and then evaporated to dryness. The residue obtained is crystallised in water. The crystals are then filtered and subsequently dried. 1.3 g of the expected dibenzoyltartrate are obtained, m.p. (MK): 90°–94° C.; yield: 45%.

NMR (DMSO d6)

$^1$H spectrum 7.95 ppm (d,4H); 7.65 ppm (t,2H); 7.5 ppm (t,4H); 6.9 ppm (s,1H); 6.45 ppm (s,1H); 5.7 ppm (s,2H); 5.3 ppm (t,1H); 4.45 ppm (t,2H); 3.65 ppm (d,2H); 3.4 ppm (m,1H); 3.1 ppm (t,2H); 2.9 ppm (m,4H); 2.7 ppm (m,2H); 2.05 ppm (m,1H); 1.8 to 1.5 ppm (m,9H); 0.8 ppm (t,3H).

EXAMPLE 10

(7RS)-7-[N-(2-methylprop-2-enyl)-N-propylamino]-5,6,7,8-tetrahydronaphtho[2,3-dihydrofuran and its (dl)-dibenzoyltartrate This compound is obtained using the general method A of Example 9, but with replacement of the 4-bromo-2-methylbut-2-ene with 3-bromo-2-methylprop-2-ene. The resulting dibenzoyltartrate melts (MK) at 98°–105° C.; yield: 47%.

NMR (300 MHz, DMSO d6)

$^1$H spectrum 8.0 ppm (d,4H); 7.7 ppm (t,2H); 7.55 ppm (t,4H); 6.9 ppm (s,1H); 6.45 ppm (s,1H); 5.75 ppm (s,2H); 5.05 and 4.95 ppm (2s,2H); 4.45 ppm (t,2H); 3.3 ppm (s,2H); 3.05 ppm (m and t,3H); 2.5 to 2.8 ppm (m,6H); 2.0 ppm (m, 1H); 1.6 ppm (s,1H); 1.75 ppm (s,3H); 1.45 ppm (m,2H); 0.85 ppm (t,3H).

EXAMPLE 11

(7RS)-7-[(2E)-N-(but-2-enyl)-N-propylamino]-5,6,7,8-tetrahydronaphtho[2,3-b]2,3-dihydrofuran and its (dl)-dibenzoyltartrate This compound is obtained using the general method A of Example 9 but with replacement of the 4-bromo-2-methylbut-2-ene with 1-bromobut-2-ene and with stirring for 24 hours at 25° C. The expected (dl)-dibenzoyltartrate melts (MK) at 90°–95° C.; yield: 68%.

NMR (DMSO d6).

$^1$H spectrum 8.0 ppm (d,4H); 7.65 ppm (t,2H); 7.55 ppm (m,4H); 6.9 ppm (s,1H); 6.45 ppm (s,1H); 5.85 and 5.55 ppm (2m,2H); 5.7 ppm (s,2H); 4.45 ppm (t,2H); 3.45 ppm (d,2H); 3.35 ppm (m,1H); 3.05 ppm (t,2H); 2.85 ppm (m,4H); 2.65 ppm (m,2H); 2.1 ppm (m,1H); 1.8 to 1.5 ppm (m,6H); 0.8 ppm (t,3H).

EXAMPLE 12

(7RS)-7-[N-(2,2-dicyclopropylethythyl)-N-propylamino]-5,6,7,8-tetrahydronaphtho[2,3-b]2,3-dihydrofuran, and its (dl)-dibenzoyltartrate This compound is obtained using the general method A of Example 9 but with replacement of the 4-bromo-2-methylbut-2-ene with 1-iodo-2,2-dicyclopropylethane. The resulting dibenzoyltartrate melts (MK) at 90°–95° C., yield: 40%.

NMR (DMSO d6)

$^1$H spectrum 7.95 ppm (d,4H); 7.65 ppm (t,2H); 7.5 ppm (m,4H); 6.9 ppm (s,1H); 6.45 ppm (s,1H); 5.7 ppm (s,2H); 4.45 ppm (t,2H); 3.5 ppm (m,1H); 3.3–2.6 ppm (m,10H); 2.15 ppm (m,1H); 1.9–1.5 ppm (m,5H); 0.85 ppm (t,3H); 0.65 ppm (t,3H); 0.35 to 0.1 ppm (2m,8H).

EXAMPLE 13

(7RS)-7-{N-[3-(4-acetamidophenyl)propyl]-N-propylamino}-5,6,7,8-tetrahydronaphtho-2,3-b]2,3-dihydrofuran and its (dl)-dibenzoyltartrate This compound was obtained using the general method A of Example 9, but with replacement of the 4-bromo-2-methylbut-2-ene with 3-(4-acetamidophenyl)-1-iodopropane. The resulting dibenzoyltartrate melts (K) at 130°–134° C.; yield: 61%.

EXAMPLE 14

(7RS)-7-[N-(3,3-dicyclopropylpropyl)-N-propylamino]-5,6,7,8-tetrahydronaphtho[2,3-b]2,3-dihydrofuran and its (dl)-dibenzoyltartrate General method B
Step B1: Formation of the amide (7RS)-7-[N-(3,3-dicyclopropylpropionyl)-N-propylamino]-5,6,7,8-tetrahydronaphtho[2,3-b]2,3-dihydrofuran A solution of 1.7 g (10.3 mmole) of 3,3-dicyclopropylpropionic acid chloride is added at 0° C. to a solution of 1.6 g (7.0 mmole) of 7-(N-propylamino)-5,6,7,8-tetrahydronaphtho[2,3-b]2,3-dihydrofuran in 50 ml of dichloromethane in the presence of 2.4 ml (2 equivalents) of N,N-diisopropylethylamine. The whole is stirred for the night at 25° C. and then diluted with water, and the organic phase is extracted and washed with (1N) HCl then $H_2O$, dried over $MgSO_4$, filtered, and evaporated to dryness. 4 g of a product are obtained which are purified by flash chromatography on silica (eluant: $CH_2Cl_2$ 100%) to yield 2.5 g of amide in the form of an oil; yield: 100%.

Step B2: Reduction with $LiAlH_4$ (7RS)-7-[N-(3,3-dicyclopropylpropyl)-N-propylamino]-5,6,7,8-tetrahydronaphtho[2,3-b]2,3-dihydrofuran and its (dl)-dibenzoyltartrate 2.0 g (5.4 mmol) of the amide of Step B1 in 50 ml of anhydrous tetrahydrofuran are added at 0° C. to a suspension of 302 mg (8.0 mmol) of $LiAlH_4$ in 40 ml of anhydrous tetrahydrofuran The temperature is allowed to rise to 25° C. and the whole is stirred overnight at room temperature and hydrolysed with water. The salts are filtered and the filtrate is evaporated to dryness. 1.9 g Of a product is obtained which is purified by flash chromatography on silica (eluant: $CH_2Cl_2$—$CH_3OH$: 95-5) to yield 1.6 g of base in the form of an oil.

42.5 ml (1 equivalent) of a 2% solution of (dl)-dibenzoyltartaric acid in $C_2H_5OH$ are added to 800 mg of base (2.2 mmol) dissolved in 30 ml of ethanol. The whole is stirred for 15 minutes and then evaporated to dryness. The residue obtained is crystallised in water. The crystals are then filtered and subsequently dried. 1.5 g of the expected (dl)-dibenzoyltartrate are obtained. m.p. (MK): 120°–148° C.; yield: 93%.

NMR (DMSO d6)

¹H spectrum: 7.95 ppm (d,4H); 7.65 ppm (t,2H); 7.5 ppm (t,4H); 6.9 ppm (s,1H); 6.45 ppm (s,1H); 5.7 ppm (s,2H); 4.45 ppm (t,2H); 3.5 ppm (m,1 H); 3.3 to 2.6 ppm (m,10H); 2.15 ppm m,1H); 1.9 to 1.5 ppm (m,5H); 0.85 ppm (t,3H); 0.65 ppm (m,3H); 0.35–0.1 ppm (2m8H).

EXAMPLE 15

(7RS)-7-[N-(2-cyclopropylethyl)-N-propylamino]-5,6,7,8-tetrahydronaphtho[2,3-b]2,3-dihydrofuran, and its hydriodide.

This compound is obtained using the general method B of Example 14.

Step B1

(7RS)-7-[N-(2-cyclopropylacetyl)-N-propylamino]-5,6,7,8-tetrahydronaphtho[2,3-b]2,3-dihydrofuran This compound is obtained using the general method B—Step B1 of Example 14, but with replacement of the 3,3-dicyclopropylpropionic acid chloride with 2-cyclopropylacetic acid chloride; yield: 55%.

Step B2

(7RS)-7-[N-(2-cyclopropylethyl)-N-propylamino]-5,6,7,8-tetrahydronaphtho[2,3-b]2,3-dihydrofuran and its hydriodide This compound is obtained using the general method B—Step B2 of Example 14 except that, for the formation of the salt, the base is dissolved in chloroform and the 2% solution of (dl)-dibenzoyltartaric acid in $C_2H_5OH$ is replaced with a (0.15N) hydriodic acid solution in chloroform. The product is crystallised in ethyl acetate. The hydriodide obtained melts (MK) at 144°–148° C.; yield: 40%.

NMR (DMSO d6)

¹H spectrum 6.95 ppm (s,1H); 6.5 ppm (s,1H); 4.4 ppm (t,2H); 3.65 ppm (m,1H); 3.4 to 2.6 ppm (m,10H); 2.2 to 1.85 ppm (2m,2H); 1.8 to 1.5 ppm (m,4H); 0.95 ppm (t,3H); 0.75 ppm (m,1H); 0.45 to 0.15 ppm (2m,4H).

EXAMPLE 16

(7RS)-7-[N-(2-cyclopentylethyl)-N-propylamino]-5,6,7,8-tetrahydronaphtho[2,3-b]2,3-dihydrofuran and its (dl)-dibenzoyltartrate This compound is obtained using the general method B—Step B1 and Step B2 of Example 14.

Step B1

(7RS)-7-[N-(2-cyclopentylacetyl)-N-propylamino]-5,6,7,8-tetrahydronaphtho[2,3-b]2,3-dihydrofuran This compound is obtained using the general method B—Step B1 of Example 14 but with replacement of the 3,3-dicyclopropylpropionic acid chloride with 2-cyclopentylacetic acid chloride; yield: 100%.

Step B2

(7RS)-7-[N-(2-cyclopentylethyl)-N-propyl amino]-5,6,7,8-tetrahydronaphtho[2,3-b]2,3-dihydrofuran and its (dl)-dibenzoyltartrate This compound is obtained using the general method B—Step B2 of Example 14. The dibenzoyltartrate obtained melts (MK) at 95°–100° C.; Yield: 59%.

NMR (DMSO d6)

¹H spectrum 7.95 ppm (d,4H); 7.65 ppm (m,2H); 7.5 ppm (m,4H); 6.9 ppm (s,1H); 6.45 ppm (s,1H); 5.7 ppm (s,2H); 4.45 ppm (t,2H); 3.5 ppm (m,1H); 3.1 ppm (t,2H); 3.1 to 2.6 ppm (2m, 8H); 2.15 ppm (m,1H); 1.9 to 1.4 ppm (m,12H); 1.1 ppm (m,2H); 0.85 ppm (t,3H).

EXAMPLE 17

(7RS)-7-{N-[4-(p-bromobenzamide)-butyl-N-propylamino}-5,6,7,8-tetrahydronaphtho[2,3-b]2,3-dihydrofuran, and its hydrochloride 3.3 g (14.2 mmole) of 7-(N-propylamino)-5,6,7,8-tetrahydronaphtho[2,3-b]2,3-dihydrofuran are dissolved in 80 ml of 1,2-dichloroethane. 4.2 g (15.7 mmole) of (p-bromobenzamide)butyraldehyde, and then 0.8 ml (14.2 mmole) of acetic acid are added. The whole is cooled to +10° C. and 4.5 g (21.3 mmole) of sodium triacetoxy borohydride are added. The whole is stirred for one night at room temperature. 100 ml of water are added, and the organic phase is extracted, dried over $MgSO_4$, filtered and evaporated to dryness. 7 g of a product are obtained which are purified by flash chromatography on silica (eluant $CH_2Cl_2$—$CH_3OH$—$NH_4OH$: 95-5-0.5) to yield 2 g of base in the form of an oil.

Those 2 g (4.1 mmol) of base are dissolved in 100 ml of ether and 20 ml of ethyl acetate, then 2 ml (5.0 mmol) of a 2.5N ethereal hydrogen chloride solution are added. The solid which precipitates is filtered and dried. 1.4 g of the expected hydrochloride, which melts (MK) at 100°–115° C., are obtained; yield: 20%.

NMR (DMSO d6)

¹H spectrum 10.1 ppm (m,NH+); 8.7 ppm (t,NH); 7.85 ppm (d,2H); 7.7 ppm (d,2H); 7.0 ppm (s,1H); 6.5 ppm (s,1H); 4.5 ppm (t,2H); 3.6 ppm (m,1H); 3.5 to 2.7 ppm (m,2H); 2.3 ppm (m,1H); 2.0 to 1.5 ppm (m,7H); 1.0 ppm (t,3H).

EXAMPLE 18

(7RS)-7-{N-[4-(cyclohexylamide)butyl]-N-propylamino}-5,6,7,8-tetrahydronaphtho[2,3-b]2,3-dihydrofuran and its (dl)-dibenzoyltartrate.

This compound is prepared according to the method described in Example 17 but with replacement of the 4-(p-bromobenzamide)butyraldehyde with 4-(cyclohexylamide) butyraldehyde. The expected dibenzoyltartrate melts (MK) at 108°14 111° C.; yield: 34%.

EXAMPLE 19

(7RS)-7-{N-[4-(p-fluorobenzamide)butyl]-N-propylamino}-5,6,7,8-tetrahydronaphtho[2,3-b]2,3-dihydrofuran and its (dl)-dibenzoyltartrate This compound is prepared according to the method described in Example 17 but with replacement of the 4-(p-bromobenzamide)butyraldehyde with 4-(p-fluorobenzamide)butyraldehyde. The expected dibenzoyltartrate melts (MK) at 108°–114° C.; yield: 19%.

EXAMPLE 20

(7RS)-7-{N-[4-(m-trifluoromethylbenzamide)butyl]-N-propylamino}-5,6,7,8-tetrahydronaphtho[2,3-b]2,3-dihydrofuran and its (dl)-dibenzoyltartrate This compound is prepared according to the method described in Example 17 but with replacement of the 4-(p- bromobenzamide)butyraldehyde with 4-(m-trifluoromethyl) butyraldehyde. The dibenzoyltartrate melts (MK) at 100°14 105° C.; yield: 38%.

EXAMPLES 21-25

The compounds forming the subject of the following Examples were also prepared by proceeding according to the method of Example 17, using appropriate starting materials:

21) (7RS)-7-{N-[4-(p-cyanobenzamide)butyl]-N-propylamino-}-5,6,7,8-tetrahydronaphtho[2,3-b]2,3-dihydrofuran, the dibenzoyltartrate of which melts (MK) at 112°-117° C.

22) (7RS)-7-{N-[3-(p-bromobenzamide)propyl]-N-propylamino}5,6,7,8-tetrahydronaphtho[2,3-b]2,3-dihydrofuran, the dibenzoyltartrate of which melts (MK) at 116°-124° C.

23) (7RS)-7-{N-[4-(o-bromobenzamide)butyl-]-N-propylamino}-5,6,7,8-tetrahydronaphtho[2,3-b]2,3-dihydrofuran, the dibenzoyltartrate of which melts (MK) at 112°-115° C.

24) (7RS)-7-{N-[4-(p-trifluoromethylbenzamide)butyl]-N-propylamino}-5,6,7,8-tetrahydronaphtho[2,3-b]2,3-dihydrofuran, the dibenzoyltartrate of which melts (MK) at 102°-108 ° C.

25) (7RS)-7-{N-[3-(p-cyanobenzamide)propyl]-N-propylamino}-5,6,7,8-tetrahydronaptho[2,3-b]2,3-dihydrofuran, the dibenzoyltartrate of which melts(MK) at 129°-136° C.

EXAMPLE 26

(7RS)-7-[N-(2-cyclobutylethyl)-N-propylamino]-5,6,7,8-tetrahydronaphtho[2,3-b]2,3-dihydrofuran, and its (dl)-dibenzoyltartrate General method C
Step C1

(7RS)-7-[N-(2-cyclobutylacetyl)-N-propylamino]-5, 6,7,8-tetrahydronaphtho[2,3-b]2,3-dihydrofuran This compound is obtained using the general method B—Step B1 of Example 14 but with replacement of the 3,3-dicyclopropylpropionic acid chloride with 2-cyclobutylacetic acid chloride. The expected product melts (K) at 84°-86° C., yield: 41%.

Step C2

(7RS)-7-[N-(2-cyclobutylethyl)-N-propylamino]-5,6, 7,8-tetrahydronaphtho[2,3-b]2,3-dihydrofuran and its (dl)-dibenzoyltartrate 2.6 ml (4 equivalents) of $BH_3.(CH_3)_2S$ (10M) are added to 2.3 g (7.0 mmol) of the amide of Step C1 dissolved in 200 ml of anhydrous tetrahydrofuran. The mixture is heated at reflux for 2 hours, cooled to 0° C., and 20 ml of $CH_3OH$—HCl (2.2N) are cautiously added. The reaction mixture is stirred for one night at room temperature and then evaporated to dryness. The residue is taken up in 100 ml of water. The pH is adjusted to 8 by adding NaOH (1N) and extracted with ethyl acetate. The organic phase is dried over $MgSO_4$, filtered and evaporated to dryness. 2 g of a product are obtained which are purified by flash chromatography on silica (eluant: $CH_2Cl_2$—$CH_3OH$: 95-5) to yield 1.2 g of base in the form of an oil. 29.9 ml (1 equivalent) of a 2% solution of (dl)-dibenzoyltartaric acid in $C_2H_5OH$ are added to 500 mg of base (1.6 mmol) dissolved in 30 ml of ethanol. The whole is stirred for 15 minutes and then evaporated to dryness. The residue obtained is crystallised in water. The crystals are then filtered and subsequently dried. 950 mg of the expected dibenzoyltartrate are obtained, m.p. (MK): 105°-110° C., yield: 45%.

NMR (DMSO d6)

$^1H$ spectrum 7.95 ppm (d,4H); 7.65 ppm (t,2H); 7.5 ppm (t,4H); 6.95 ppm (s,1H); 6.45 ppm (s,1H); 5.7 ppm (s,2H); 4.45 ppm (t,2H); 3.45 ppm (m,1H); 3.1 ppm (t,2H); 2.85 ppm (m,4H); 2.85 to 2.7 ppm (m,4H); 2.25 to 2.17 ppm (3m,13H); 0.85 ppm (t,3H).

EXAMPLE 27

(7RS)-7-[N-(2-cyclohexylethyl)-N-propylamino]-5, 6,7,8-tetrahydronaphtho[2,3-b]2,3-dihydrofuran, and its (dl)-dibenzoyltartrate Step C1

(7RS)-7-[N-(2-cyclohexylacetyl)-N-propylamino]-5, 6,7,8-tetrahydronaphtho[2,3-b]2,3-dihydrofuran This compound is obtained using the general method B—Step B1 of Example 14 but with replacement of the 3,3-dicyclopropylpropionic acid chloride with 2-cyclohexylacetic acid chloride, yield: 95%.

Step C2

(7RS)-7-[N-(2-cyclohexylethyl)-N-propylamino]-5, 6,7,8-tetrahydronaphtho[2,3-b]2,3-dihydrofuran This compound is obtained using the general method C—Step C2 of Example 26, m.p. (MK): 95°-102° C.; yield: 20%.

NMR (DMSO d6)

$^1H$ spectrum 8.0 ppm (d,4H); 7.65 ppm (t,2H); 7.5 ppm (m,4H); 6.9 ppm (s,1H); 6.45 ppm (s,1H); 5.65 ppm (s,2H); 4.45 ppm (t,2H); 3.4 ppm (m,1H); 3.1 ppm (t,2H); 3.1 to 2.6 ppm (m,8H); 2.1 ppm (m,1H); 1.7 to 1.0 ppm (m,5H); 1.4 to 0.7 ppm (m,11H); 0.8 ppm (t,3H).

EXAMPLE 28

(7RS)-7-[N-(cis-2-methylcyclopropylmethyl)-N-propylamino]-5,6,7,8-tetrahydronaphtho[2,3-b]2,3-dihydrofuran and its (dl)-dibenzoyltartrate This compound is obtained using the general method C described in Example 26, but with the use in Step C1 of cis-2-methylcyclopropanecarboxylic acid chloride instead of 2-cyclobutylacetic acid chloride. The expected dibenzoyltartrate melts (MK) at 95°-100° C.; yield: 38%.

EXAMPLE 29

(7RS)-7-{N-[2-(biphenyl-4-yl)ethyl]-N-propylamino}-5,6,7,8-tetrahydronaphtho[2,3-b]2,3-dihydrofuran and its (dl)-dibenzoyltartrate This compound is obtained using the general method C described in Example 26, but with the use in Step C1 of 2-(biphenyl-4-yl)acetic acid chloride instead of 2-cyclobutylacetic acid chloride. The expected dibenzoyltartrate melts (MK) at 100°105° C.; yield: 35%.

EXAMPLE 30

Pharmacological Study

STUDY OF THE BINDING OF THE COMPOUNDS OF THE INVENTION TO HUMAN $D_2$ AND $D_3$ RECEPTORS EXPRESSED IN CHO CELLS

1/ Material and method. Cell culture

CHO (Chinese Hamster Ovary) cells were transfected in a stable manner by the gene coding for the human dopamine $D_2$ or $D_3$ receptor according to methods known from the literature. The native cells are deficient in the enzyme DHFR (DiHydroFolate Reductase). Those cells are cultured in a vessel at 37° C. in a humid atmosphere of 5% $CO_2$: 95% air. The transfections were carried out using Lipofectine (Gibco). The CHO cells, cotransfected with the human $D_2$ receptor and the gene for resistance to phleomycin, were selected for their resistance to the presence of that antibiotic in the culture medium. The cells transfected with the human $D_3$ receptor were selected in a medium lacking in hypoxanthine/thymidine, in the presence of methotrexate. The compositions of the culture media used are, for CHO—$D_2$: DMEM (Dulbecco's Modified Eagle Medium) supplemented with 10% foetal calf serum and hypoxanthine/thymidine and, for CHO—$D_3$: DMEM supplemented with 10% dialysed foetal calf serum. The confluent cells are harvested and the membranes are then prepared.

Preparation of the membranes

After a few minutes in the presence of 0.2% trypsin, the cells are recovered and centrifuged at 2000 g for 5 minutes. The cell mass, resuspended in 10ram tris-HCl buffer, pH 7.5, containing 5 mM $MgSO_4$, is then distilled over Polytron®. The homogenate is then centrifuged at 50 000 g for 15 minutes, and the mass is resuspended by gentle sonication in an incubation buffer of the following composition: 50 mM tris-HCl, pH 7.5, containing 120 mM NaCl, 5 mM KCl, 2 mM $CaCl_2$ and 5 mM $MgCl_2$. The membranes are then divided into aliquots and preserved at −80° C. until the day of the experiment.

Binding experiments

The incubation is carried out in polypropylene tubes at a final volume of 400 μl containing:

100 μl of [$^{125}$I]-iodosulpride (Amersham) at 0.1 and 0.2 nM for the $D_2$ and $D_3$ receptors respectively.

100 μl of buffer (total tubes)

or

100 μl of raclopride 10 μM (non-specific binding)

or

100 μl of compound.

200 μl of membrane preparation containing the $D_2$ or $D_3$ receptors, in a buffer to which 0.2% BSA (bovine serum albumin) has been added.

The ranges of concentration of each compound include at least 7 points determined in triplicate; each experiment is repeated at least twice.

The incubation, which lasts 30 minutes at 30° C., is terminated by rapid filtration in a Brandle apparatus, followed by three consecutive washes with tris-HCl buffer, pH 7.4, containing 120 m M NaCl. The filters recovered are then counted with a gamma counter.

Analysis of the results

The $IC_{50}$, which represents the concentration that gives a 50% inhibition of the binding of the radioligand, is calculated by non-linear regression (Prism Graph method). The Ki value is derived from the formula $Ki=IC_{50}/(1+L/Kd)$ where L is the concentration of [$^{125}$I]-iodosulpride used in the experiment and Kd its dissociation constant. The results are expressed in the form of pKi (pKi=−logKi).

For the human $D_2$ and $D_3$ receptors the Kds are equal, respectively, to 0.5 and 1.31 nM.

2/Results

The affinities for the human $D_3$ receptor in the case of the products particularly representative of the invention are listed in the following Table.

| Products tested | | pKi (human $D_3$) |
|---|---|---|
| Compounds of the present application | | |
| Example N° | [form tested] | |
| 3 | [(dl)-dibenzoyltartrate] | 8.65 |
| 6 | [hydrochloride] | 8.94 |
| 7 | [base] | 8.46 |
| 13 | [(dl)-dibenzoyltartrate] | 8.45 |
| Compounds described in the patent specifications EP 0 286 515 and EP 0 286 516 | | |
| (structure 1) O—naphthalene—$NH_2$ [hydrochloride] | | 6.80 |
| (structure 2) O—naphthalene—$NH_2$ [hydrochloride] | | 6.41 |
| (structure 3) O—naphthalene—N(H)—CH$_2$CH$_2$—O— [hydrochloride] | | 6.12 |
| (structure 4) O—naphthalene—N(H)—$CF_3$ [hydrochloride] | | 5.00 |
| (structure 5) O—naphthalene—N($CH_3$)$_2$ [hydrochloride] | | 6.68 |
| (structure 6) O—naphthalene—N($CH_3$)($CH_2$-cyclohexyl) [hydrochloride] | | 6.82 |
| (structure 7) O—naphthalene—N(H)($CH_2$-phenyl) | | 5.93 |
| Reference product AJ 76* | | 7.16 |

*AJ 76 = [cis-(+)-1S,2R]-5-methoxy-1-methyl-2-n-propylaminotetralin

The comparison of the results obtained with the tested products of the present invention and those obtained with the products described in the Patent Specifications EP 0 286 5

15 and 0 286 516 demonstrate that the modifications carried out to the substituents of the amine function have brought about a very significant increase in activity as regards the affinity for the $D_3$ receptors.

Furthermore, all of the products of the present invention demonstrate affinities for the $D_2$ receptor that are from 10 to 100 times lower than those shown for the $D_3$ receptor, which is not true of the products described in the Patent Specifications EP 0 286 515 and 0 286 516. The same applies also to the reference product AJ 76, which has a selectivity of only 2 for the $D_3$ receptor compared with the $D_2$ receptor.

We claim:

1. A compound selected from the group consisting of those of formula I:

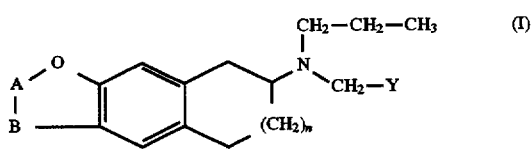

wherein:

A–B represents CH=CH or $CH_2$–$CH_2$;

n represents zero or one; and

Y represents:

($C_2$–$C_{10}$)alkenyl in straight or branched chain;

ω-(cycloalkyl)alkyl, ω-(methylcycloalkyl)alkyl, or ω,ω-(dicycloalkyl)alkyl in each of which each cycloalkyl contains 3 to 7 carbon atoms inclusive, and the alkyl moiety contains 1 to 4 carbon atoms inclusive in straight or branched chain;

or a group of formula:

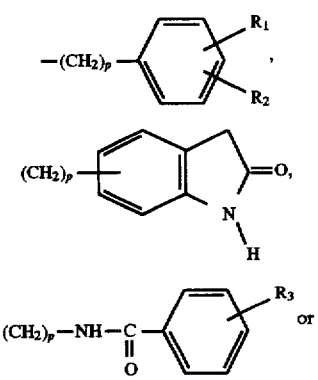

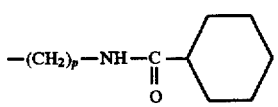

wherein:

p is an integer of 1 to 4 inclusive, $R_1$ represents hydrogen, halogen, hydroxy, or methoxy, $R_2$ represents halogen, hydroxy, ($C_1$–$C_5$)alkoxy, phenyl, —NH—CO—$CH_3$, —NH—CO—$CF_3$, or —NH—$SO_2$—$CH_3$, and $R_3$ represents halogen, ($C_1$–$C_5$)alkoxy, trifluoromethyl, cyano, phenyl, p-aminophenyl, or p-acetylphenyl;

in racemic form or in the form of optical isomers; and addition salts thereof with pharmaceutically-acceptable acids.

2. A compound of claim 1 which is selected from the group consisting of (7RS)-7-{N-[3-((3H)-indol-2-on-5-yl)propyl]-N-propylamino}-5,6,7,8-tetrahydronaphtho[2,3b]2,3-dihydrofuran and its (dl)-dibenzoyltartrate.

3. A compound of claim 1 which is selected from the group consisting of (7RS)-7-[N-(2-cyclopentylethyl)-N-propylamino]-5,6,7,8-tetrahydronaphtho[2,3-b]2,3-dihydrofuran and its (dl)-dibenzoyltartrate.

4. A compound of claim 1 which is selected from the group consisting of (7RS)-7-{N-[3-(4-acetamidophenyl)propyl]-N-propyl-amino}-5,6,7,8-terahydronaphtho[2,3-b]2,3-dihydrofuran and its (dl)-dibenzoyltartrate.

5. A compound of claim 1 which is selected from the group consisting of (7RS)-7-{N-[4-(p-fluorobenzamide)butyl]-N-propylamino}-5,6,7,8-tetrahydronaphtho[2,3-b]2,3-dihydrofuran and its (dl) dibenzoyltartrate.

6. A method for treating a living animal body afflicted with a condition selected from Parkinson's disease, memory disorders, disorders associated with drug abuse, depression, and psychotic states, comprising the step of administering to the said living animal body an amount of a compound of claim 1 which is effective for the alleviation of said condition.

7. A pharmaceutical composition useful in treating depression, comprising as active ingredient an effective amount of at least one of the compounds according to claim 1, together with one or more pharmaceutical-acceptable excipients.

* * * * *

UNITED STATES PATENT AND TRADEMARK OFFICE
CERTIFICATE OF CORRECTION

PATENT NO. : 5,665,765
DATED : September 9, 1997
INVENTOR(S) : J-L Peglion, J. Vian, A. Dessinges, M. Millan, V. Audinot Page 1 of 3

It is certified that error appears in the above-indentified patent and that said Letters Patent is hereby corrected as shown below:

Title Page, [75] Inventors, line 3: "Le Peco" should read -- Le Pecq --.

Column 4, line 40: "(7R8)" should read -- (7RS) --.

Column 4, line 55: "flouorophenyl)ethyl]" should read -- fluorophenyl)ethyl] --.

Column 5, line 50: Delete the "(" at the end of the line.

Column 5, line 51: Insert -- ( -- at the beginning of the line.

Column 7, line 11: "dibenzoyltataric" should read --dibenzoyltartaric--.

Column 7, line 28: Insert -- 2,3-b] -- after the "[" and before "2,3-dihydrofuran".

Column 7, line 41: " (S,1H)" should read -- (m,1H); --.

Column 7, line 62: "dicyclopropylethythyl)" should read -- dicyclopropylethyl) --.

UNITED STATES PATENT AND TRADEMARK OFFICE
CERTIFICATE OF CORRECTION

PATENT NO. : 5,665,765
DATED : September 9, 1997
INVENTOR(S) : J-L Peglion, J. Vian, A. Dessinges, M. Millan, V. Audinot Page 2 of 3

It is certified that error appears in the above-indentified patent and that said Letters Patent is hereby corrected as shown below:

Column 8, line 58: "Of" should read -- of --.

Column 9, line 54: Insert -- 2,3-b] -- after the "[" and before "2,3-dihydrofuran".

Column 11, line 2: Delete "14" at the end of the line and insert a dash.

Column 11, line 17: "butyl-]-N-" at the end of the line should read -- butyl]-N- --.

Column 11, line 39: Insert -- 2,3-b] -- after the "[" and before "2,3-dihydrofuran".

Column 13, line 9: "Cell culture" should begin a new paragraph.

Column 13, line 32: "10ram" should read -- 10mM --.

Column 15, line 29: Insert a "comma" after "dicycloalkyl)alkyl".

UNITED STATES PATENT AND TRADEMARK OFFICE
CERTIFICATE OF CORRECTION

PATENT NO. : 5,665,765
DATED : September 9, 1997
INVENTOR(S) : J-L Peglion, J. Vian, A. Dessinges, M. Millan, V. Audinot Page 3 of 3

It is certified that error appears in the above-indentified patent and that said Letters Patent is hereby corrected as shown below:

Column 15, line 30: Delete the "comma" after the word "inclusive".

Column 16, line 47: The word "pharmaceutical" should read -- pharmaceutically --.

Signed and Sealed this

Twenty-fifth Day of November, 1997

Attest:

BRUCE LEHMAN

Attesting Officer

Commissioner of Patents and Trademarks